(12) United States Patent
Jacquemyns

(10) Patent No.: US 9,011,147 B2
(45) Date of Patent: Apr. 21, 2015

(54) DENTIST TOOL

(75) Inventor: Evelyne Jacquemyns, Sint-Martens-Latem (BE)

(73) Assignee: Viax Dental Technologies, LLC, Miami, FL (US)

( * ) Notice: Subject to any disclaimer, the term of this patent is extended or adjusted under 35 U.S.C. 154(b) by 56 days.

(21) Appl. No.: 13/524,383

(22) Filed: Jun. 15, 2012

(65) Prior Publication Data

US 2012/0270176 A1     Oct. 25, 2012

Related U.S. Application Data

(63) Continuation of application No. 12/364,216, filed on Feb. 2, 2009, now abandoned.

(51) Int. Cl.
*A61C 3/02* (2006.01)
*A61C 13/00* (2006.01)

(52) U.S. Cl.
CPC ............ *A61C 13/0004* (2013.01); *A61C 3/02* (2013.01)

(58) Field of Classification Search
CPC ........................................ A61C 3/02
USPC ...................................... 433/75, 76
See application file for complete search history.

(56) References Cited

U.S. PATENT DOCUMENTS

| | | | | |
|---|---|---|---|---|
| 472,004 | A | * 3/1892 | Sweet et al. | ..................... 433/75 |
| 1,407,840 | A | 2/1922 | Cruttenden | |
| 3,407,503 | A | * 10/1968 | Nealon | ............................. 433/76 |
| 3,445,935 | A | * 5/1969 | Marshall | ........................... 433/51 |
| 4,144,645 | A | * 3/1979 | Marshall | ....................... 433/223 |
| 4,504,230 | A | 3/1985 | Patch | |
| 4,778,387 | A | 10/1988 | Komatsu | |
| 4,941,826 | A | * 7/1990 | Loran et al. | ..................... 433/51 |

(Continued)

FOREIGN PATENT DOCUMENTS

| | | |
|---|---|---|
| CN | 1678254 A | 10/2005 |
| DE | 4012327 A1 | 10/1991 |

(Continued)

OTHER PUBLICATIONS

P. Hahn, Fracture strengh of 3-unit inlay bridges after thermo-mechanical fatigue in a chewing simulator, http://www.gapless.de/, Oct. 25, 2001, 2 pages.

(Continued)

*Primary Examiner* — Ralph Lewis
(74) *Attorney, Agent, or Firm* — Lerner, David, Littenberg, Krumholz & Mentlik, LLP

(57) ABSTRACT

A method for producing a dentist tool for use in removing tooth structure is provided. The method includes acquiring three-dimensional data relating to a shape of a tooth and part of a neighboring tooth. The method includes processing the data to determine an overlay fitting the tooth and part of the neighboring tooth. The method further includes processing the data to determine the tooth structure to be removed from the tooth to prepare the tooth for further treatment. The method includes determining first and second guiding edges such that the two edges are spaced apart a distance of at least 0.5 mm and configured to enable a dentist cutting tool to be guided by simultaneously contacting the first and second guiding edges to enable a guided removal of at least partially the predetermined part of tooth structure. The method includes producing the determined overlay having the determined guiding edges.

26 Claims, 3 Drawing Sheets

(56) References Cited

U.S. PATENT DOCUMENTS

| | | |
|---|---|---|
| 4,997,369 A | 3/1991 | Shafir |
| 5,118,294 A | 6/1992 | Kurer |
| 5,224,049 A | 6/1993 | Mushabac |
| 5,257,184 A | 10/1993 | Mushabac |
| 5,343,391 A | 8/1994 | Mushabac |
| 5,347,454 A | 9/1994 | Mushabac |
| 5,448,472 A | 9/1995 | Mushabac |
| 5,545,039 A | 8/1996 | Mushabac |
| 5,562,448 A | 10/1996 | Mushabac |
| 5,569,578 A | 10/1996 | Mushabac |
| 5,575,656 A * | 11/1996 | Hajjar .......................... 433/219 |
| 5,725,376 A * | 3/1998 | Poirier .......................... 433/172 |
| 5,800,168 A | 9/1998 | Cascione et al. |
| 6,030,211 A | 2/2000 | Sandhaus |
| 6,257,892 B1 | 7/2001 | Worthington |
| 6,447,296 B2 | 9/2002 | Worthington |
| 6,786,726 B2 | 9/2004 | Lehmann et al. |
| 7,097,451 B2 * | 8/2006 | Tang .............................. 433/76 |
| 7,108,511 B1 | 9/2006 | Shatkin |
| 7,172,424 B2 | 2/2007 | Wu |
| 7,287,982 B2 | 10/2007 | Riley et al. |
| 7,346,417 B2 | 3/2008 | Luth et al. |
| 7,367,801 B2 | 5/2008 | Saliger |
| 7,572,125 B2 | 8/2009 | Brajnovic |
| 7,658,610 B2 | 2/2010 | Knopp |
| 7,905,726 B2 | 3/2011 | Stumpel |
| 8,011,927 B2 | 9/2011 | Berckmans, III et al. |
| 2001/0036617 A1 | 11/2001 | Karmaker et al. |
| 2005/0095554 A1 | 5/2005 | Wilkinson |
| 2005/0282106 A1 | 12/2005 | Sussman et al. |
| 2006/0127848 A1 | 6/2006 | Sogo et al. |
| 2008/0312659 A1 | 12/2008 | Metzger et al. |
| 2009/0291417 A1 | 11/2009 | Rubbert et al. |
| 2010/0173259 A1 | 7/2010 | Vogel et al. |
| 2010/0192375 A1 | 8/2010 | Jacquemyns |
| 2010/0196842 A1 | 8/2010 | Jacquemyns |

FOREIGN PATENT DOCUMENTS

| | | |
|---|---|---|
| EP | 1547544 A1 | 6/2005 |
| WO | 0234154 | 5/2002 |
| WO | WO 2007/104842 A1 * | 9/2007 |

OTHER PUBLICATIONS

International Search Report and Written Opinion for Application No. PCT/US2012/039569 dated Sep. 14, 2012.
Chinese Office Action for Application No. 201080014124.5 dated Sep. 18, 2013.
Japanese Office Action for Application No. 2011-546876 dated Dec. 20, 2013.
Canadian Office Action for Application No. 2,750,698 dated Apr. 10, 2013.
Australian Examination Report for Application No. 2010209671 dated Jan. 29, 2014.
Russian Office Action for Application No. 2011136473 dated Feb. 22, 2014.
Mexican Office Action for Application No. MX/a/2011/008128 dated Apr. 9, 2014.
Japanese Office Action for Application No. 2011-546876 dated Aug. 5, 2014.

* cited by examiner

DENTIST TOOL

CROSS-REFERENCE TO RELATED APPLICATIONS

The present application is a continuation of U.S. patent application Ser. No. 12/364,216, filed Feb. 2, 2009, the disclosure of which is incorporated herein by reference.

SUMMARY OF THE INVENTION

The present invention concerns a method for producing a dentist tool formed by an overlay to be used by a dentist in removing tooth structure, said method comprising the steps of:

acquiring three-dimensional data relating to a shape of at least one predetermined tooth and at least a part of a neighbouring tooth of said predetermined tooth;

processing said three-dimensional data with a computer so as to determine an overlay fitting said tooth and fitting at least said part of said neighbouring tooth;

determining guiding means within said overlay, suitable for guiding a dentist cutting tool;

producing said determined overlay having said determined guiding means.

The present invention further concerns a dentist tool obtained by the application of the described method.

When a patient needs a crown, bridge, onlay, inlay, veneer, or other restoring and/or aesthetic tooth treatment, conventionally, during an initial office visit, the dentist identifies the needs of the patient and determines an appropriate treatment. During subsequent visits, in case the tooth comprises damaged and/or infected tooth structure, the dentist removes this tooth structure and reconstructs the tooth as much as possible using conventional techniques. Thereafter, the dentist performs the final preparation of the tooth for further treatment by removing tooth material, which is to be interpreted as original tooth structure and reconstructed tooth structure, with a dental cutting tool such as a high-speed drill. Relying upon eyesight and expertise, the dentist uses the drill to shape the tooth in a form that is suitable for further treatment, in particular a form onto which a crown, bridge, onlay, inlay, veneer or other tooth restoring part can be mounted. Then, the dentist takes an impression of the dental arch in which the prepared tooth is located, and sends the impression to the dental laboratory to have the dental technician make the restoration part. Using the impression of the prepared tooth, the dental technician produces a restoration part that matches the colour, geometrical and material specifications, and sends it to the dentist. At the patient's final visit, the dentist adjusts the restoration part as necessary before fitting it in place.

Such a dentist tool is disclosed in EP1547544. The known dentist tool decreases the impact of the experience and expertise of the dentist onto the treatment, and it is used by a dentist in boring an artificial tooth root cavity. In EP1547544, guiding means, formed by a cylindrical hole, for guiding a drill in a straight-forward way, is provided. In such a manner an artificial tooth root cavity can be bored with greater precision even by a less experienced dentist. Moreover a suitable root cavity position can be calculated based on the information processed by the computer, so as to form in the most optimal way a cavity in the jaw bone.

A drawback of the known dentist tool is that it can only be used by a dentist in boring holes into the jaw bone. This dentist tool is not suitable to be used by a dentist in preparing a tooth for further treatment.

It is an object of the present invention to provide method for producing a dentist tool that is suitable for being used by a dentist in preparing a tooth for further treatment.

To this end, a dentist tool according to the present invention is characterized in that said method comprises the further steps of:

before determining said guiding means, determining a predetermined part of tooth structure to be removed from said tooth so as to prepare said tooth for further treatment;

determining at least two guiding edges of which a first and a second guiding edge are spaced apart from each other by a distance of at least 0.5 mm, said guiding edges being part of said guiding means (7), said guiding edges being configured so as to enable said dentist cutting tool to be guided by simultaneously contacting said first and said second guiding edge in such a manner as to enable a guided removal of at least partially said predetermined part of tooth structure.

The determination of a predetermined part of tooth structure to be removed results in that this does not any more depend on the skills of the dentist. Depending on the individual dental situation of a patient, the computer is programmed to determine an optimal way for shaping the tooth into a shape that is suitable for further treatment. Determining and producing guiding edges into an overlay, which guiding edges are suitable for simultaneously contacting the dentist cutting tool, allows the cutting tool to be guided along a well determined path in an at least partially predetermined way. The overlay, having the guiding edges, accurately indicates onto the tooth the part to be removed from the tooth as determined by the computer. Moreover the tool according to the invention is provided to assist the dentist in removing tooth structure as the tool allows a dentist to remove at least part of a predetermined part of tooth structure.

It is to be noted that the term fitting is not to be interpreted in the narrow sense that the overlay should closely surround the teeth. It moreover should be interpreted as that an overlay should surround the teeth so as to be adequately in contact with the teeth and so that, once applied, it will not be released even if certain pressure, due to a normal use of the overlay, is applied.

In a preferred embodiment of the invention, said first and said second guiding edge are designed for simultaneously contacting said dentist cutting tool at contacting points being longitudinally distanced from each other by said distance, said guiding edges thereby defining a guiding surface along which said dentist cutting tool is to be guided.

By simultaneously contacting two guiding edges with a cutting tool at contacting points being longitudinally distanced from each other, the cutting tool can be guided at least partially in a predetermined way. Preferably the cutting tool moves along the two guiding edges and thereby defines a guiding surface. This surface comprises the two guiding edges, and a cutting tool can be guided along this surface. This allows an accurate guiding in two dimensions.

Preferably, in determining said guiding means, a guiding groove is determined, which defines a path extending in a surface of said overlay and suitable for guiding said dentist cutting tool along said path in such a manner as to enable a guided removal of at least partially said predetermined part of tooth structure.

The two guiding edges, being distanced from each other, can be located one on the one side and the other on the other side of the path thereby defining the path between the two guiding edges. To this purpose, the distance between the two guiding edges should be substantially equal to a diameter of the cutting tool. Using the dentist cutting tool by simultaneously contacting the two guiding edges and following the path allows a guidance of the cutting tool at least in two dimensions. Considering a longitudinal cutting tool, the surface defined by the two guiding edges in this configuration will be substantially perpendicular to the direction of the cutting tool in use.

The two guiding edges, being distanced from each other, can also be both located on one side of the path. At least a third guiding edge will then define the other side of the path. Considering a longitudinal cutting tool in this configuration, the surface defined by the two guiding edges will be substantially parallel to the direction of the cutting tool in use. The third guiding edge in this configuration will provide a further guidance to the cutting tool thereby increasing the accuracy of the process of removal of tooth structure. Using the dentist tool by simultaneously contacting the two guiding edges and following the path in this configuration allows a guidance of the cutting tool in two dimensions and a guidance of inclination of the cutting tool.

Preferably, the method comprises the further steps of:

determining a tooth restoration part having an inner shape so as to fit a remaining part of tooth structure of said tooth, and having an outer shape so as to fit together with remaining neighbouring teeth;

producing said tooth restoration part.

An advantage of the method according to the invention is that the shape of the remaining part of tooth structure of the prepared tooth is known in advance due to the guided removal of tooth structure. This improves further treatment, such as preparing a temporary or final inlay, onlay, bridge, crown or veneer in advance based on the three-dimensional data. This results in that less office visits are required, as the dentist can both prepare the tooth and mount the tooth restoration part onto the prepared tooth in one single visit. This way of working does not only save time and thus costs, also the inconvenience for the patient is strongly decreased. Furthermore the chances that a prepared tooth gets contaminated, and the resulting complications, are reduced to a minimum.

Preferably, said predetermined part is determined by:

firstly determining a tooth restoration part having an outer shape so as to fit together with remaining neighbouring teeth, and having an inner shape compatible with said outer shape;

secondly determining a shape of remaining tooth structure so that said tooth restoration part having said inner shape fits said shape of remaining tooth structure;

thirdly determining said predetermined part as being the part of tooth structure to be removed so as to have said shape of remaining tooth structure left.

Starting with determining a tooth restoration part instead of, as conventionally, preparing the tooth, has an advantage. A tooth restoration part can be determined having an outer shape so as to optimally fit together with remaining neighbouring teeth. Procedures for determination of such an outer shape are known to the person skilled in the art. An inner shape is then determined, which inner shape is compatible with said outer shape. Criteria for being compatible depend on the material that is to be used and mainly concern strength parameters, production parameters and parameters relating to the mounting of the restoration part onto the tooth and/or teeth. Preferably the inner shape is determined in such a manner that a minimum amount of material is required to produce the tooth restoration part. This at its turn results in that the remaining tooth structure, required to fit to this inner shape, is as large as possible, namely, the more material of a restored tooth is tooth restoration material, the less material of that restored tooth is tooth structure. Then the predetermined part can be determined as being the part of tooth structure to be removed so as to have said shape of remaining tooth structure left. Thus first determining the tooth restoration part, results in that a minimum of tooth structure is to be removed from the tooth and maximum conservation of the original tooth structure. As it is best to maintain as much of the original tooth structure, this is an advantage.

In a further step, the determined tooth restoration part having the determined outer and inner shape, can be produced. This results in that less office visits are required, as the dentist can prepare the tooth and mount the tooth restoration part onto the prepared tooth in one single visit, having the advantageous as described above.

Preferably said removal of tooth structure is to be performed in a plurality of stages in which said guiding means is provided to guide said cutting tool in a first stage of said plurality of stages, and at least one further guiding means is provided to guide said cutting tool in at least one further stage, the method further comprising the steps of:

determining said at least one further guiding means (7) each comprising at least two further guiding edges of which a further first and a further second guiding edge are spaced apart from each other by a distance of at least 0.5 mm, said further first and said further second guiding edges being provided for simultaneously contacting said dentist cutting tool thereby guiding said dentist cutting tool in such a manner as to enable a guided removal of at least partially said predetermined part of tooth structure;

producing at least one further overlay each having one of said at least one further guiding means.

Producing a plurality of overlays instead of just one overlay provides a further flexibility in the method for producing the dentist tool. Different overlays can be provided for guiding a dentist cutting tool along different sides of the tooth to be prepared, so that for example a circumferential path can be defined by using multiple overlays each defining a different segment of the circumferential path. Multiple overlays furthermore allow to use different dental cutting tools, which is necessary in some cases. Different overlays can be provided for preparing a tooth in multiple stages, in which for example a first stage is provided to smoothen the upper part of the tooth, a second and a third stage are provided to cut away the longitudinal and transversal sides of the tooth, and a fourth and fifth stage are provided to round off the edges between the longitudinal and transversal sides each at a different side of the tooth. Preparing a tooth in stages allows each overlay to be designed having guiding edges which are particularly determined for guiding the cutting tool in a particular way characterised by the particular stage.

BRIEF DESCRIPTION OF THE DRAWINGS

The invention will now be described in more details with respect to the drawings illustrating some preferred embodiments of the invention. In the drawings.

DETAILED DESCRIPTION

Figure 1:
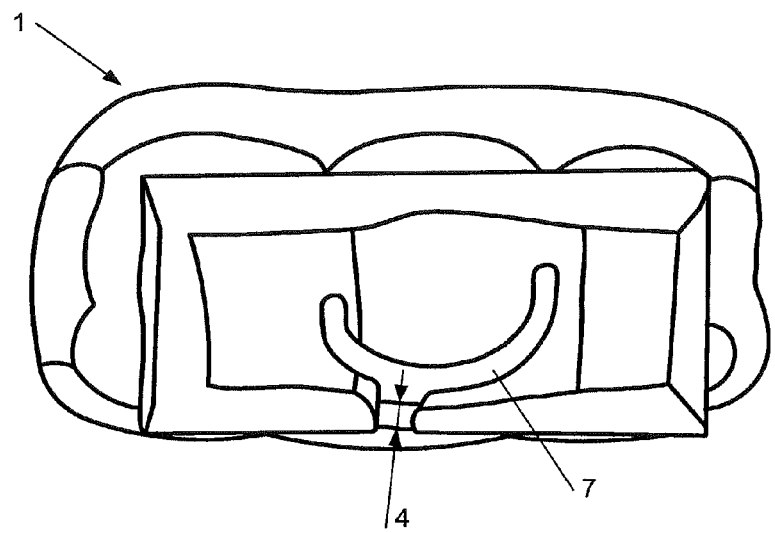
FIG. 1 shows a top view of an overlay with a guiding groove according to the invention.

In the drawings a same reference number has been allocated to a same or analogous element.

The terms "lower", "upper" etc. and derived directional terms such as "horizontal" and "vertical" are based on a normal configuration of an overlay as shown in the drawings, wherein the overlay fits onto teeth with their root extending vertically downward. The term dentist in this text is not to be interpreted restrictive and can also be read as dental technician, dental assistant, dental auxiliary, dental therapist, dental designer etc.

Figure 2:
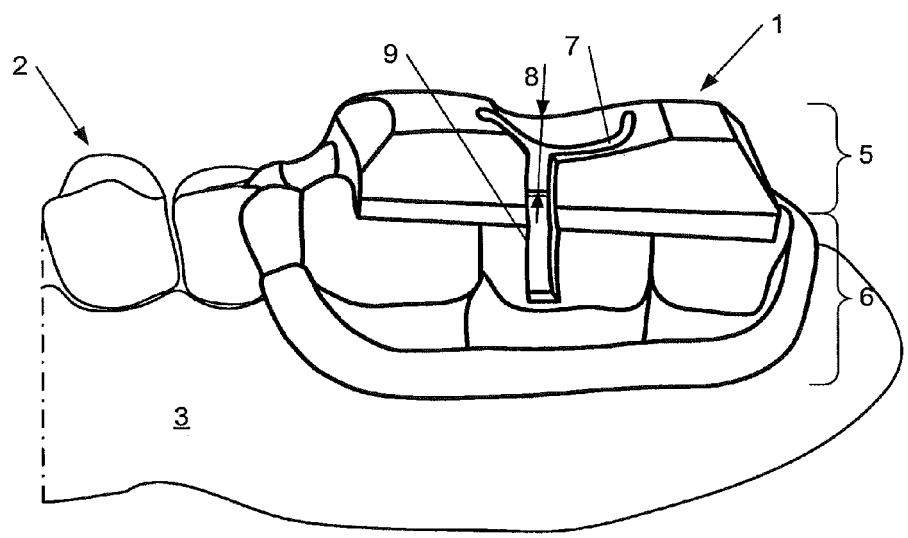
FIG. 2 shows a side view of an overlay with a guiding groove placed onto a patient's teeth.

The invention provides a method for producing a dentist tool formed by an overlay 1 to be used by a dentist in removing tooth structure. Furthermore, the invention provides an overlay 1 obtainable by this method. FIGS. 1 and 2 show such an overlay 1 arranged onto the teeth 2 of a patient. Preferably, the invention provides a method for producing the dentist tool and a tooth restoration part in such a manner that the tooth restoration part will fit the tooth that is prepared using the dentist tool.

The dentist tool according to the invention is preferably used by a dentist in preparing a tooth for a restoration such as placing inlays and onlays, crowns, bridges, and veneers. Such restoration requires a restoration part to be produced in order to fit the tooth after the latter has been prepared. Using the dentist tool according to the invention results in that the shape of the prepared tooth, which conventionally is only known after preparation, is determined in advance. Based on this knowledge, a restoration part can be produced in advance so that this restoration part is available to the dentist even before he or she starts preparing the tooth, and can be mounted directly after preparation of the tooth. This results in that the patient suffers less inconvenience, in particular that the number of visits to the dentist are reduced. Furthermore the chances that a prepared tooth gets contaminated, and the resulting complications, are reduced to a minimum.

Preferably, preparing a tooth for further treatment is performed onto a substantially healthy tooth. When a tooth is damaged or infected, the damaged and/or infected parts of the tooth will have to be removed first, and the tooth will have to be reconstructed before preparing the tooth for further treatment. This minimizes the chance that an infection develops underneath a tooth restoration part. This also maximizes the lifetime of the tooth restoration part as the basis for the tooth restoration part, namely the tooth, does not contain damaged parts any more.

Several methods are known for acquiring three-dimensional data from a patient's dentition. Such data can be retrieved by processing photographs taken from the patient's dentition. Another method is making a physical impression of the dentition and then scanning this impression with a CAD/CAM 3D scanning device. For what concerns the present invention, any appropriate method for acquiring three-dimensional data can be used.

After acquiring the three-dimensional data of the tooth, this data gets processed by a computer so as to determine an overlay 1 fitting the teeth 2 of the patient. To this end, the inner shape of the overlay preferably corresponds to the outer shape of the tooth to be prepared and to the outer shape of at least part of a neighbouring tooth. Overlay should fit the teeth in such a manner that once the overlay is placed onto the teeth, it will only come off by applying a sufficiently high force to the overlay. During preparation of the tooth, small forces may be applied to the overlay, which preferably should not modify the position of the overlay on the teeth. Preferably, the overlay 1 extends over the teeth 2 so as to also cover part of the gingiva 3 for stability purpose and protection purpose. As the dentist will use the overlay 1 for removing tooth material, it is advantageous that the overlay 1 is located onto the tooth in a stable way. As an example, an overlay 1 closely fitting the tooth, two neighbouring teeth, and part of the gingiva 3, ensures that a dentist can arrange and maintain the overlay in a stable position during removal of tooth structure. When the overlay 1 covers a part of the gingiva 3, at least this part of the gingiva 3 will be protected during the process of removing tooth structure.

It is to be noted that an overlay 1 according to the invention can cover multiple teeth at once and can be provided to be used by a dentist in preparing a plurality of teeth using one single overlay 1. This can be advantageous in the process of preparing teeth for placing veneers. Such an overlay comprises guiding means, as will be explained further, for each tooth that needs to be prepared.

The determined overlay 1 has a thickness 4 that mainly depends on the required strength thereof, and thus also the material it will be made of. An overlay 1 according to the invention can have a constant overall thickness 4. A substantially constant overall thickness is preferred for an overlay to be used by a dentist in preparing a tooth or teeth for placing veneers. An overlay to be used for preparing a tooth for placing a bridge or a crown preferably comprises an upper, guiding part 5, and a lower, supporting part 6. The supporting part 6 of the overlay 1 will ensure that the overlay 1 can be arranged in a stable way onto the teeth 2, whereas the guiding part 5 of the overlay 1 will guide the dentist cutting tool and preferably will also determine the maximal penetration depth of the cutting tool in the tooth. To this end, the thickness of the guiding part 5 of the overlay 1 will preferably be determined case by case together with the determination of the guiding means 7, as will be explained further. The thickness 4 of the supporting part 6 of the overlay 1 can be more freely chosen depending on the preferences of the dentist and/or the programmation of the computer.

After acquiring the three-dimensional data, this data gets also processed by a computer so as to determine a predetermined part of tooth structure to be removed from the tooth by the dentist. The predetermined part will be determined in view of the further treatment. If a particular shape of the prepared tooth is required for allowing further treatment, the predetermined part will be chosen so that after preparation of the tooth, this particular shape will remain.

Determining the predetermined part depends on many parameters and will differ from case to case. Parameters are the location of the tooth in the mouth of the patient, amount and location of the damaged tooth structure, distance of the tooth to neighbouring teeth, etc. In a preferred embodiment, the computer will also take into account the different parts of the tooth such as the enamel, denting, pulp, cementum, etc. in determining the predetermined part.

According to the invention, the computer is programmed to determine the predetermined part of tooth structure to be removed without assistance of a dentist except for what concerns the input of the initial data of the tooth. However also according to the invention, the computer can be programmed to determine the predetermined part in cooperation with a dentist, where for example the dentist decides on some parameters. This cooperation can be established by visualizing data relating to the tooth onto a computer display and allowing the dentist at least to enter one parameter relating to the preparation of the tooth. Preferably a preview of the tooth is visualized onto the computer display together with a preview of a simulation of the prepared tooth, so as to allow a dentist to see the impact of chosen parameters onto the prepared tooth. The latter feature provides a larger degree of freedom to the dentist and allows a less experienced dentist to consult a more experienced dentist about a case, based on the data in the computer. In this manner, the method for producing a dentist tool according to the invention allows a less experienced dentist to decide on a further treatment and prepare a tooth for further treatment with a same quality as if he or she was an experienced dentist.

In another embodiment, the computer is programmed to determine the predetermined part of tooth structure to be removed in several phases. At the end of each phase, the computer proposes a simulated solution to the dentist and requests for approval or correction of the proposed solution.

Preferably the predetermined part will be determined in several steps. In a first step, the outer shape of the tooth restoring part is to be determined so that the tooth restoring part fits with the remaining teeth and fits into the dental arch of the patient. A bite lift or other corrective amendment can be directly integrated into the design of the outer shape. Then, based on this determined outer shape, an inner shape gets determined that is compatible with the outer shape. In such a manner, a tooth restoration part can be determined having an optimal outer shape, and an optimal construction in the sense that it is strong enough and a minimum of material is needed. In a following step, the shape of remaining tooth structure is to be determined so that the inner shape of the tooth restoring part fits the remaining tooth structure after removal of tooth structure. In a final step, the predetermined part of tooth structure is determined as the part of tooth structure to be removed to have the shape of remaining tooth structure left. This way of working allows determining the outer shape of the tooth restoring part using best fit programs. Conventionally, the dentist will not follow the steps in the succession as mentioned above. The dentist will work the other way around, as the dentist will need to know the shape of the prepared tooth to determine the inner shape of the restoration part, after which the dentist will determine an appropriate outer shape. Firstly determining the tooth restoration part, according to a preferred embodiment of the invention, results in that a minimum of tooth structure is to be removed from the tooth and a maximum conservation of the original tooth structure can be obtained.

Once the predetermined part has been determined, guiding means can be determined. The purpose of the guiding means is to guide a dentist cutting tool, i.e. a drill, so that the cutting tool removes at least a part of the predetermined part. To this end, it will be understood that in some cases, the dimensions of the dentist cutting tool, such as the length, diameter, cross-sectional form, etc. will be determining for which movement is to be made with the cutting tool to remove a certain part of tooth structure. It will also be understood that in many cases, it will not be sufficient to make one single movement for removing all the predetermined part. Via computer calculation and/or simulation, one or more movements can be determined for removing the predetermined part of tooth structure. It is to be understood that a movement in this context does not only relates to a two-dimensional position, but relates to the movement of the cutting tool in all its aspects such as horizontal movement, vertical movement and tilt movement.

The guiding means according to the invention comprise at least two guiding edges 11, 12 (FIG. 3-6). Two of these guiding edges 11, 12 are spaced apart from each other with a distance d of at least 0.5 mm. The guiding edges 11, 12 are provided to simultaneously contact the cutting tool 10 thereby guiding the cutting tool 10 at least partially into a predetermined movement. It is to be understood in this context that a surface having a length and having a width which are at least 0.5 mm can be considered as the said at least two guiding edges 11, 12. Namely, the two outer edges of the surface are provided to simultaneously contact the cutting tool 10, and are spaced apart with a distance d of at least 0.5 mm.

Preferably the two guiding edges 11, 12 are spaced apart from each other with a distance d of at least 1 mm, more preferably of at least 2 mm and most preferably of at least 3 mm. Increasing the distance d between the two edges 11, 12 will increase the guiding quality as it will be much easier for a dentist to control the cutting tool 10 onto larger guiding means.

Figure 3:
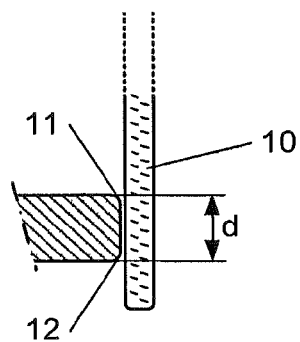
FIG. 3 shows a cross section of part of an overlay with guiding means according to one embodiment of the invention and a cutting tool.

The guiding edges 11, 12 are provided in such a manner as to be simultaneously contacted by the cutting tool at two contacting points. As illustrated in FIG. 3, preferably these contacting points 11, 12, considered on the cutting tool 10, are longitudinally spaced apart by the distance d. When the cutting tool 10 is arranged substantially perpendicular to the guiding edges, the distance between the contacting points will be substantially the same as the distance d between the guiding edges. FIG. 3 illustrates a cutting tool 10 lying simultaneously against the two guiding edges 11, 12. The guiding edges 11, 12 in this configuration define a surface along which the cutting tool 10 can be guided.

Figure 4:
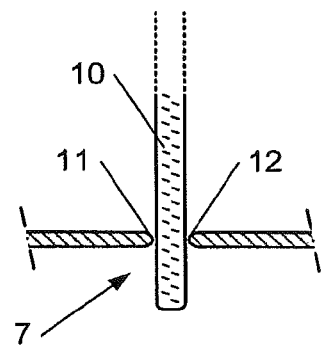
FIG. 4 shows a cross section of part of an overlay with guiding means according to another embodiment of the invention and a cutting tool.

However the guiding edges 11, 12 can also simultaneously contact the cutting tool 10 at two contacting points being located each at one side of the cutting tool 10, as illustrated in FIG. 4. In this configuration, the guiding edges 11, 12 define a guiding groove in which the cutting tool 10 can be guided. The guiding groove 7 is preferably determined so as to define a path laying in the upper surface of the overlay 1. The groove 7 is provided for guiding a dentist cutting tool along this path, and to this end, the groove 7 extends through the overlay so as to form a communication between the inside of the overlay and the outer environment. When more than one path is to be followed for removing the predetermined part, multiple guiding grooves 7 will have to be determined.

Figure 5:
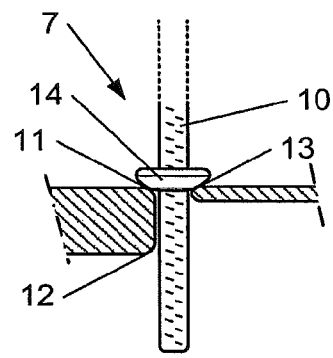
FIG. 5 shows a cross section of part of an overlay with guiding means according to the invention and a cutting tool.

A combination of these two mentioned configurations is illustrated in FIG. 5. In this figure, a first and second guiding edge 11, 12, being the two guiding edges that are spaced apart, can be seen on the left hand side, which edges define a guiding surface. A third guiding edge 13 can be seen on the right hand side, which edge defines, together with the first and second guiding edge 11, 12, a path. This configuration therefore allows a cutting tool to be guided into both a horizontal movement and a tilt.

As can be seen in FIG. 5, the cutting tool 10 preferably comprises a collar 14 mounted onto the cutting tool 10. Preferably at least one of the guiding edges 11, 12, 13 is provided to guide the collar 14 of the cutting tool 10 thereby guiding the cutting tool 10 into a predetermined vertical position or height or depth. As can be seen in the FIG. 5, the guiding groove 7 defining a horizontal path, furthermore defines a predetermined height 8 for each horizontal location of the cutting tool, so as to guide the cutting tool 10 along a horizontal path and in a predetermined tilt, and also guiding the cutting tool in the vertical way.

Figure 6:
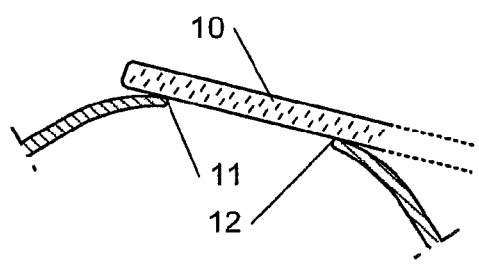
FIG. 6 shows a cross section of part of an overlay with guiding means according to a further embodiment of the invention and a cutting tool.
Figure 7A:
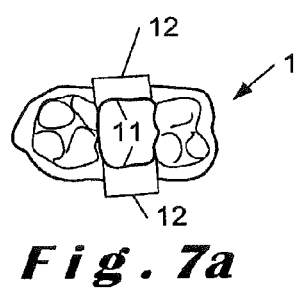
FIG. 7 shows a set of overlays to be used by a dentist in preparing a tooth for mounting a crown or bridge.

FIG. 6 illustrates a variant on the embodiment shown in FIG. 3, and shows the guiding edges 11, 12, which are provided to simultaneously contact the cutting tool at two contacting points being longitudinally distanced from each other. In this embodiment, tooth structure can be removed that is located in between the two guiding edges 11, 12. In particular in preparing a tooth for placing veneers, this embodiment will be used.

For mounting a crown or a bridge, the tooth is to be shaped into a truncated pyramid having rounded edges. To this end the outer and upper part of the tooth are to be removed. This removal of tooth structure can be guided by the dentist tool according to the invention.

Figure 8:
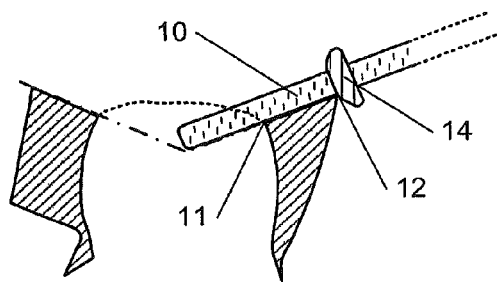
FIG. 8 shows a cross-section of the overlay shown in FIG. 7*a*.

Preferably the removal of tooth structure for preparing a tooth for mounting a crown or a bridge is performed in several stages shown in FIG. 7. In a first stage, shown in FIG. 7a and FIG. 8, the upper part of the tooth gets smoothened. This can be done using an overlay having guiding edges 11, 12 as illustrated in FIG. 6. However in practice, it is preferred that the upper part gets shaped into a V-form. To this end, the upper part preferably gets smoothened using two guiding means as illustrated in FIG. 3, which guiding means are located on both sides of the tooth in such a manner that said guiding means are provided guide said cutting tool to cut said upper part into a V-shape.

Figure 7B:
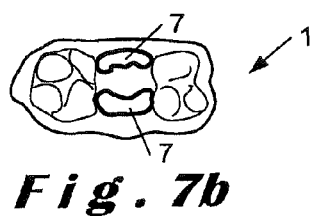
Figure 7C:
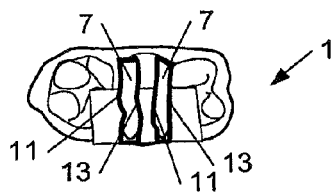

In a second and a third stage, shown in FIGS. 7b and 7c, the longitudinal and transversal sides of the tooth get cut, so as to obtain a truncated pyramid form. The cutting of these sides can be guided by overlays having guiding means as illustrated in FIG. 3, 4 or preferably FIG. 5. Preferably one overlay comprises two such guiding means each defining a path extending in the surface of the overlay, the paths extending parallel to each other, each on one side of the tooth.

Figure 7D:
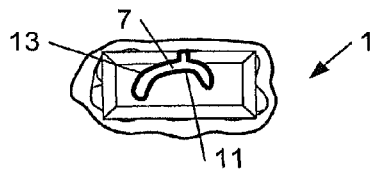
Figure 7E:
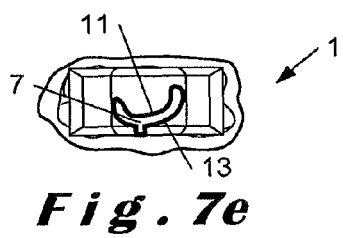

In a fourth and fifth stage, shown in FIGS. 7d and 7e, the edges of the pyramid get rounded. Rounding these edges can be guided by an overlay as shown in FIGS. 1 and 2. Such an overlay comprises a path extending in the surface of the overlay and defining a segment of a circle. Each side of the path is defined by a guiding surface having at least two guiding edges, as illustrated in FIG. 3. The height of the guiding part 5 of the overlay 1 is defined so as to guide the cutting tool 10 in a predetermined vertical position.

In this succession of stages, the first stage could be executed as the last stage instead of as the first. However tests have shown that starting with smoothening the upper part of the tooth is advantageous in the process of preparing the tooth.

Once the overlay 1 and the guiding means are determined, the determined overlay 1 having the determined guiding means can be produced. This can be done by any known means such as a CAD/CAM system, rapid prototyping or 3D printing. When multiple guiding means have been determined, multiple overlays 1 can be produced each comprising one or several guiding means.

The overlay 1 has, as already mentioned above, a lower, supporting part 6 and an upper, guiding part 5. As can be seen in the figures, the guiding part 5 has a certain thickness 8, which defines the height 8 of the path and enables the cutting tool to be guided in the vertical way. Preferably the supporting part 6 and/or guiding part 5 comprises a vertical opening 9 from the side to the guiding groove 7, provided to serve as an entrance into the guiding groove 7 for a dental cutting tool. In particular when a cutting tool has a tip portion that has a diameter that is larger than the diameter of the main portion of the cutting tool, for example a high-speed drill with a tip in the form of a ball, this opening is advantageous. Entering such a cutting tool into the guiding groove 7 via the upper part of the overlay would at least partially widen the guiding groove 7 thereby at least partially taking away its possibility to firmly guide the cutting tool along the predetermined path. Furthermore a side entrance 9 is preferred over an entrance via the upper part as it will be easier to enter the cutting tool in a controlled manner into the guiding groove 7.

When a guiding groove 7 is determined to form a circular path in the horizontal plane, it will be preferred to split up this path into several segments, and produce multiple overlays 1 each having a guiding groove 7 corresponding to one segment of this path. This will result in a set of overlays 1 which can be used by a dentist one after the other to remove tooth structure following this circular path. Each overlay 1 of the set of overlays 1 will guide the cutting tool along a particular side of the tooth.

In the embodiment where the predetermined part is not determined based on the shape of the tooth restoration part, the latter can be determined based on the data in the computer. Outer shape of the tooth restoration part can be determined in several ways, all known to the person skilled in the art. A bite lift or other corrective amendment can be directly integrated into the design of the outer shape. A first possibility is to shape the tooth restoration part so that it resembles the outer shape of the original tooth. A second possibility is to shape the tooth restoration part so that it fits with neighbouring teeth. A third possibility is a combination of the first and second, and modifies the shape of the original tooth to better fit with the neighbouring teeth. Inner shape of the tooth restoration part will be determined based on the simulation of the preparation of the tooth. As the tooth will be prepared in a guided manner, it is known in advance what the shape will be of the prepared tooth. The inner shape of the tooth restoration part will be chosen so that it fits the shape of the prepared tooth.

Preferably the method according to the invention further comprises the step of producing a tooth restoration part.

Similar to the determination of the predetermined part, a tooth restoration part can be determined by a computer without any interaction of a dentist. However it will be preferred that the computer determines the tooth restoration part in cooperation with a dentist, for example in a way as described above. The computer can, in this process of determining a tooth restoration part, perform predetermined clinical checks and alert the dentist in case the tooth restoration part does not meet the standard norms. This will enable a dentist to design a tooth restoration part in a fast and reliable manner.

The production of the tooth restoration part can be done by any means known to the skilled person such as a CAD/CAM system.

The invention claimed is:

1. Overlay for guiding a dental cutting tool to remove predetermined tooth structure from a tooth to be treated, the overlay comprising:
   an inner surface having a shape and dimensions corresponding to an outer surface of the tooth to be treated so that the inner surface is releasably fixable to the tooth to be treated;
   a first guiding edge extending through a thickness of the overlay including through the inner surface, the first guiding edge having a contour corresponding to horizontal, vertical, and tilt movements to be followed by a dental cutting tool; and
   a second guiding edge extending through the thickness of the overlay including through the inner surface and spaced apart from the first guiding edge by a distance d, the second guiding edge having a contour corresponding to the horizontal, vertical, and tilt movements to be followed by the dental cutting tool.

2. The overlay of claim 1, wherein the inner surface has a shape and dimensions so that it is releasably fixable to at least a part of a neighboring tooth of the tooth.

3. The overlay of claim 1, wherein the inner surface has a shape and dimensions so that the inner surface is releasably fixable to at least parts of a plurality of neighboring teeth, the inner surface, when fixed to the neighboring teeth, surrounding and adequately contacting the teeth so that the overlay does not release or move upon application of pressure during guiding of the cutting tool in normal use of the overlay.

4. The overlay of claim 1, wherein the distance d is at least 0.5 mm.

5. The overlay of claim 1, wherein the first and the second guiding edges are spaced apart a fixed distance at corresponding contacting points along respective lengths of the first and the second guiding edges.

6. The overlay of claim 1, wherein the first and the second guiding edges are spaced apart a fixed distance for contacting the at least one dental cutting tool at corresponding contacting points of the first and the second guiding edges.

7. The overlay of claim 1, wherein the overlay is a monolithic, inseparable structure.

8. The overlay of claim 1, wherein the first and the second guiding edges extend in a horizontal direction such that when the dental cutting tool is located at least at one position between the first and the second guiding edges and is oriented vertically, the overlay guides the dental cutting tool to follow only a horizontal movement of the horizontal, vertical, and tilt movements.

9. The overlay of claim 1, wherein the first and the second guiding edges extend in a vertical direction such that when the dental cutting tool is located at least at one position between the first and the second guiding edges and is oriented horizontally, the overlay guides the dental cutting tool to follow only a vertical movement of the horizontal, vertical, and tilt movements.

10. A dental cutting tool comprising a configuration providing it with the capacity of engaging one or more guiding edges of the overlay of claim 1.

11. Set of overlays to be used for guiding at least one dental cutting tool in removing predetermined tooth structure from a tooth to be treated, the set of overlays comprising two or more of the following overlays:
a first overlay having a shape and dimensions for guiding at least one dental cutting tool to cut away at least a portion of an upper part of a tooth based on a desired height of remaining tooth structure after removal of the upper part of the tooth;
a second overlay having a shape and dimensions for guiding at least one dental cutting tool to cut away at least a portion of a longitudinal side of the tooth;
a third overlay having a shape and dimensions for guiding at least one dental cutting tool to cut away at least a portion of a transversal side of the tooth;
a fourth overlay having a shape and dimensions for guiding at least one dental cutting tool to round off edges between the longitudinal and the transversal sides of the tooth at one side of the tooth; and
a fifth overlay having a shape and dimensions for guiding at least one dental cutting tool to round off edges between the longitudinal and the transversal sides of the tooth at the other side of the tooth opposite the one side of the tooth,
wherein each of the overlays of the set of overlays has an inner surface having a shape and dimensions so that each of the overlays is releasably fixable to the tooth to be treated.

12. The set of overlays of claim 11, wherein the inner surface of at least one overlay of the set of overlays has a shape and dimensions so that the inner surface is releasably fixable to at least a part of a neighboring tooth of the tooth.

13. The set of overlays of claim 11, wherein the inner surface of at least one overlay of the set of overlays has a shape and dimensions so that the inner surface is releasably fixable to at least parts of a plurality of neighboring teeth, the inner surface, when fixed to the neighboring teeth, surrounding and adequately contacting the teeth so that the at least one overlay does not release or move upon application of pressure during guiding of the cutting tool in normal use of such overlay.

14. The set of overlays of claim 11, wherein at least one of the overlays has the first and the second guiding edges spaced apart a fixed distance for contacting the at least one dental cutting tool at corresponding contacting points of the first and the second guiding edges.

15. A dental cutting tool comprising a configuration providing it with the capacity of engaging one or more guiding edges of an overlay present in the set of overlays of claim 11.

16. System to be used by a dentist to remove predetermined tooth structure from a tooth to be treated, the system comprising:
a dental cutting tool; and
the set of overlays of claim 11.

17. The system of claim 16, wherein one or more overlays of the set of overlays comprises:
an inner surface having a shape and dimensions corresponding to an outer surface of the tooth to be treated so that the inner surface is releasably fixable to the tooth to be treated;
a first guiding edge extending through a thickness of the overlay including through the inner surface, the first guiding edge having a contour corresponding to horizontal, vertical, and tilt movements to be followed by a dental cutting tool; and
a second guiding edge extending through the thickness of the overlay including through the inner surface and spaced apart from the first guiding edge by a distance d, the second guiding edge having a contour corresponding to the horizontal, vertical, and tilt movements to be followed by the dental cutting tool.

18. System to be used by a dentist to remove predetermined tooth structure from a tooth to be treated, the system comprising:
a dental cutting tool; and
an overlay comprising:
an inner surface having a shape and dimensions corresponding to an outer surface of the tooth to be treated so that the inner surface is releasably fixable to the tooth to be treated;
a first guiding edge extending through a thickness of the overlay including through the inner surface, the first guiding edge having a contour corresponding to horizontal, vertical, and tilt movements to be followed by the dental cutting tool; and
a second guiding edge extending through the thickness of the overlay including through the inner surface and spaced apart from the first guiding edge by a distance d, the second guiding edge having a contour corresponding to the horizontal, vertical, and tilt movements to be followed by the dental cutting tool.

19. The system of claim 18, wherein a portion of the dental cutting tool has a thickness such that the dental cutting tool simultaneously contacts the first and the second guiding edges of the overlay as the dental cutting tool moves along a path defined by the first and the second guiding edges.

20. The system of claim 18, wherein the dental cutting tool comprises a cutting portion and a collar, at least one of the first and the second guiding edges of the overlay being configured to contact the collar so as to enable the dental cutting tool to be guided by the overlay with a predetermined depth.

21. The system of claim 18, wherein the inner surface of the overlay has a shape and dimensions so that it is releasably fixable to at least a part of a neighboring tooth of the tooth.

22. The system of claim 18, wherein the first and the second guiding edges are spaced apart a fixed distance at corresponding contacting points along respective lengths of the first and the second guiding edges.

23. The system of claim 18, wherein the first and the second guiding edges are spaced apart a fixed distance for contacting the at least one dental cutting tool at corresponding contacting points of the first and the second guiding edges.

24. The system of claim 18, wherein the overlay is a monolithic, inseparable structure.

25. The system of claim 18, wherein the first and the second guiding edges extend in a horizontal direction such that when the dental cutting tool is located at least at one position between the first and the second guiding edges and is oriented vertically, the overlay guides the dental cutting tool to follow only a horizontal movement of the horizontal, vertical, and tilt movements.

26. The system of claim 18, wherein the first and the second guiding edges extend in a vertical direction such that when the dental cutting tool is located at least at one position between the first and the second guiding edges and is oriented horizontally, the overlay guides the dental cutting tool to follow only a vertical movement of the horizontal, vertical, and tilt movements.

* * * * *